US010403411B2

(12) United States Patent
Schreuder et al.

(10) Patent No.: US 10,403,411 B2
(45) Date of Patent: Sep. 3, 2019

(54) SHIELDING DEVICE

(71) Applicant: GE Healthcare Limited, Buckinghamshire (GB)

(72) Inventors: Nanno Schreuder, Zwolle-Overijssel (NL); Gerard Swiers, Zwolle-Overijssel (NL); Maikel Herbrink, Amsterdam (NL)

(73) Assignee: GE HEALTHCARE LIMITED, Buckinghamshire (GB)

( * ) Notice: Subject to any disclaimer, the term of this patent is extended or adjusted under 35 U.S.C. 154(b) by 0 days.

(21) Appl. No.: 15/765,529

(22) PCT Filed: Oct. 28, 2016

(86) PCT No.: PCT/EP2016/076039
§ 371 (c)(1),
(2) Date: Apr. 3, 2018

(87) PCT Pub. No.: WO2017/072279
PCT Pub. Date: May 4, 2017

(65) Prior Publication Data
US 2019/0080808 A1 Mar. 14, 2019

(30) Foreign Application Priority Data
Oct. 29, 2015 (GB) .................................. 1519136.4

(51) Int. Cl.
*B21B 31/07* (2006.01)
*F15B 13/02* (2006.01)
(Continued)

(52) U.S. Cl.
CPC .............. *G21F 5/018* (2013.01); *A61J 3/075* (2013.01); *G21G 1/0005* (2013.01); *G21G 4/08* (2013.01)

(58) Field of Classification Search
CPC ........ G21F 5/018; A61J 3/075; G21G 1/0005; G21G 4/08
(Continued)

(56) References Cited

U.S. PATENT DOCUMENTS 4,401,432 A 8/1983 Schwartz
7,343,724 B1 3/2008 Williams
(Continued)

FOREIGN PATENT DOCUMENTS

WO 2008049240 A1 5/2008
WO 2017072279 A1 5/2017

OTHER PUBLICATIONS

International Search Report and the Written Opinion of the International Searching Authority, or the Declaration from International Appl. No. PCT/EP2016/076039, dated Feb. 15, 2017.
(Continued)

*Primary Examiner* — Nicole M Ippolito
(74) *Attorney, Agent, or Firm* — Arent Fox LLP

(57) ABSTRACT

The present invention relates to the field of radioactive substances and in particular to a method to facilitate handling of radioactive solutions. Provided by the present invention is a device that enables preparation of capsules filled with radioactivity. More particularly, the radioactivity is suitable for use in certain radiopharmaceutical procedures. The present invention provides improved accuracy and uniformity of patient doses. Furthermore, the potential for spills and needle stick injuries is reduced and the radiation burden is reduced.

33 Claims, 9 Drawing Sheets

(51) Int. Cl.

| | |
|---|---|
| ***G21G 4/08*** | (2006.01) |
| ***G21F 5/018*** | (2006.01) |
| ***A61J 3/07*** | (2006.01) |
| ***G21G 1/00*** | (2006.01) |

(58) Field of Classification Search
USPC ......... 250/505.1, 516.1, 515.1, 517.1, 518.1, 250/519.1
See application file for complete search history.

(56) References Cited

U.S. PATENT DOCUMENTS

2003/0141210 A1* 7/2003 Yanke .................... A61J 1/00 206/364
2006/0086909 A1* 4/2006 Schaber ................. G21F 5/018 250/506.1
2007/0219505 A1* 9/2007 Zehner ................ A61M 5/1785 604/198
2008/0210890 A1* 9/2008 Fago .................. A61M 5/1785 250/506.1
2008/0210892 A1* 9/2008 Wagner ................. G21F 5/015 250/515.1
2009/0292157 A1* 11/2009 Bruce ................ A61M 5/1785 600/5

OTHER PUBLICATIONS

Great Britain Search Report from GB Appl. No. GB1519136.4, dated Jul. 19, 2016.

* cited by examiner

SHIELDING DEVICE

TECHNICAL FIELD OF THE INVENTION

The present invention relates to the field of radioactive substances and in particular to handling of radioactive solutions. Provided by the present invention is a device that enables preparation of capsules filled with radioactivity. More particularly, the capsules filled with radioactivity are suitable for oral administration for use in certain radiopharmaceutical procedures.

DESCRIPTION OF RELATED ART

Radiopharmaceuticals are administered to patients either orally or by intravenous injection. One method for oral administration is via a small capsule that contains a diagnostic or therapeutic dose of the radioactive isotope. These capsules are routinely prepared in nuclear pharmacies by manually injecting a solution containing the radioactive isotope into the capsules, typically made from hard gelatin. In a known process, one large gelatin capsule and one small gelatin capsule are used for each dose prepared. Each large capsule comprises two parts and is empty, and each small capsule may contain an absorbing buffer such as Dibasic Sodium Phosphate Anhydrous USP. The required volume of a radioactive solution to produce the necessary dose in MBq or mCi is calculated based on the calibration date and radionuclidic concentration. The large capsule is pulled apart and the small capsule is placed into the bottom half of the large capsule. The volume of radioactive solution is withdrawn using a shielded syringe and then injected into the top centre of the small capsule. Then the upper part of the large capsule is secured around the bottom half so that the small capsule is contained within the large capsule. Following measurement of the patient dose in a suitable radioactivity calibration system the dose is administered to a patient.

This known filling process of capsules is manual and therefore subject to variation between individual operators. This is problematic for accuracy and uniformity of the patient doses inside the capsule. Furthermore, although shielding is mostly used around the syringe in this manual process, no shielding is provided around the capsule itself thereby giving a high radiation burden to the hands of the operator. In addition, this manual process is prone to spills and needle stick injuries.

It would therefore be desirable to have better accuracy and uniformity of patient doses, reduced radiation burden and reduced possibility of a spill or needle stick injury.

SUMMARY OF THE INVENTION

In a first aspect the present invention provides a system (1) comprising:

(i) a capsule holder (2) having a lower end (2*a*) and an upper end (2*b*) wherein said capsule holder comprises a solid base (2*c*) positioned at said lower end (2*a*), a solid body (2*d*) extending upwardly from said solid base (2*c*), and a well (2*e*) extending downwardly within said solid body (2*d*) wherein said well (2*e*) opens at the upper end (2*b*) of said capsule holder (2) and ends prior to said solid base (2*c*) and is configured to receive a lower half (3*a*) of a capsule (3), wherein said capsule holder (2) is formed from a radiation-shielding material;

(ii) a shielded needle positioner (4) having a lower end (4*a*) and an upper end (4*b*) wherein said shielded needle positioner (4) comprises a solid body (4*c*) defining a bore (4*d*) extending substantially linearly and centrally therethrough, said bore (4*d*) comprising a lower section (4*e*) opening onto said lower end (4*a*) and configured to be fitted over and contain the solid body (2*d*) of said capsule holder (2), and an upper section (4*f*) opening onto said upper end (4*b*) and configured to receive an upper half (3*b*) of a capsule (3), wherein said shielded needle positioner (4) is formed from a radiation-shielding material.

In a second aspect the present invention provides a method for filling a capsule (3) with radioactivity wherein said capsule comprises an inner shell (3*c*) and an outer shell (3*d*) wherein said outer shell (3*d*) comprises a lower diameter body (3*e*) and a greater diameter cap (3*f*) and wherein said method comprises the following steps:

(a) providing the system of the invention as defined herein;

(b) placing said lower diameter body (3*e*) into the well (2*e*) of the capsule holder (2);

(c) placing said inner shell (3*c*) into said lower diameter body (3*e*);

(d) placing the shielded needle positioner (4) over the capsule holder (2) containing the lower diameter body (3*e*) and the inner shell (3*c*) so that the solid body (2*d*) of the capsule holder (2) is contained within the lower section (4*e*) of the bore (4*d*) of the shielded needle positioner (4) and an upper half of the inner shell (3*c*) is contained within the upper section (4*f*) of the bore (4*d*) of the shielded needle positioner (4);

(e) introducing a first needle (7*a*) attached to a shielded syringe (7) containing a solution of radioactivity into the upper section (4*f*) of the bore (4*d*) at the upper end (4*b*) of said shielded needle positioner (4);

(f) injecting the solution of radioactivity into the inner shell (3*c*)

(g) removing the shielded needle positioner (4);

(h) fixing said greater diameter cap (3*f*) to said lower diameter body (3*e*) so that said inner shell (3*c*) is securely contained within said outer shell.

The present invention provides improved accuracy and uniformity of patient doses. Furthermore, the potential for spills and needle stick injuries is reduced and the radiation burden is reduced.

The invention makes filling of oral capsules with a radioactive solution safe and easy. It offers protection from radiation through shielding all around the filling process. It also ensures correct placement of the syringe and needle every time, resulting in an accurate and uniform patient dose inside the capsule. Furthermore, the inventive system allows the operator to fill the capsules faster, which also reduces the radiation burden for the operator.

The system and method of the invention are of relevance to all sites where oral capsules need to be filled with radioactive solution or another hazardous solution. In the USA there are in excess of 400 nuclear pharmacies that prepare such oral capsules that could benefit from using the present invention.

DETAILED DESCRIPTION OF THE PREFERRED EMBODIMENTS

The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components being present.

The term "capsule" as used herein is intended to refer to a pharmaceutical preparation comprising a hard or soft shell typically containing a single dose of active substance. In one embodiment said capsule is intended for oral administration. Such capsules are well known to those of skill in the art and are described in the US and European Pharmacopeias. The shell of the capsule may be made from a biodegradable material, for example gelatin, starch or other similar substances, which upon attack by digestive fluids allows the contents to be released. The consistency of the shell material may be adjusted by the addition of substances such as glycerol or sorbitol. Excipients such as surface-active agents, opaque fillers, antimicrobial preservatives, sweeteners, colouring matter authorised by the competent authority and flavouring substances may be added. The capsules may bear surface markings. Hard-shell capsules for human use come in a range of sizes from No. 5, the smallest, to No. 000, which is the largest. Size No. 00 is generally is the largest size acceptable to patients (see e.g. Chapter 6 "Pharmaceutical Calculations" 2016 Jones and Bartlett Learning; Payal Agarwal, Ed.). In certain embodiments the capsules include contents of a solid, liquid or paste-like consistency comprising one or more active substances with or without excipients such as solvents, diluents, lubricants, disintegrating agents, reducing agents, pH-adjusting agents and stabilizers. Suitably, the contents should not cause deterioration of the shell and the shell should be sealed appropriately to prevent any leakage. For the absorption and retention of a quantity of a radioactive solution, the small capsule may contain a hydroscopic crystalline powder. $^{123}I$ capsules are well-known in the art (see e.g. Chapter 34 "Iodine Chemistry and Applications" 2015 John Wiley & Sons; Tatsuo Kaiho, Ed.)

The term "solid" is used herein in connection with various components of the system of the invention and takes its ordinary meaning, i.e. firm and stable in shape.

Figure 1:
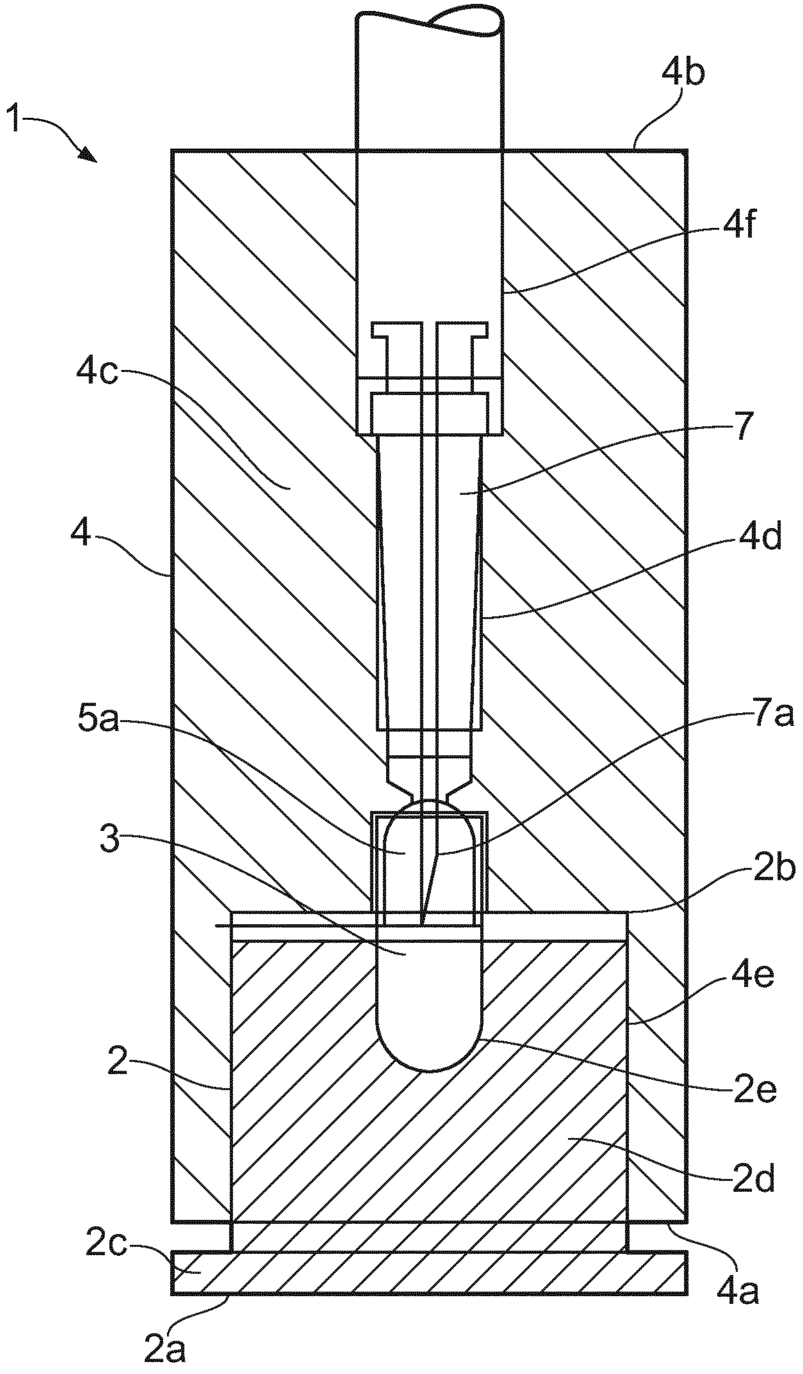
FIG. 1 is a schematic diagram of a non-limiting example of a system (1) of the present invention. A capsule holder (2) with a capsule (3) therein is shown covered by a shielded needle positioner (4). Also shown is a needle (7*a*) attached to a syringe (7) wherein the needle (7*a*) is penetrating the capsule (3) as would be the case when a radioactive solution is being injected into the capsule.
Figure 2:
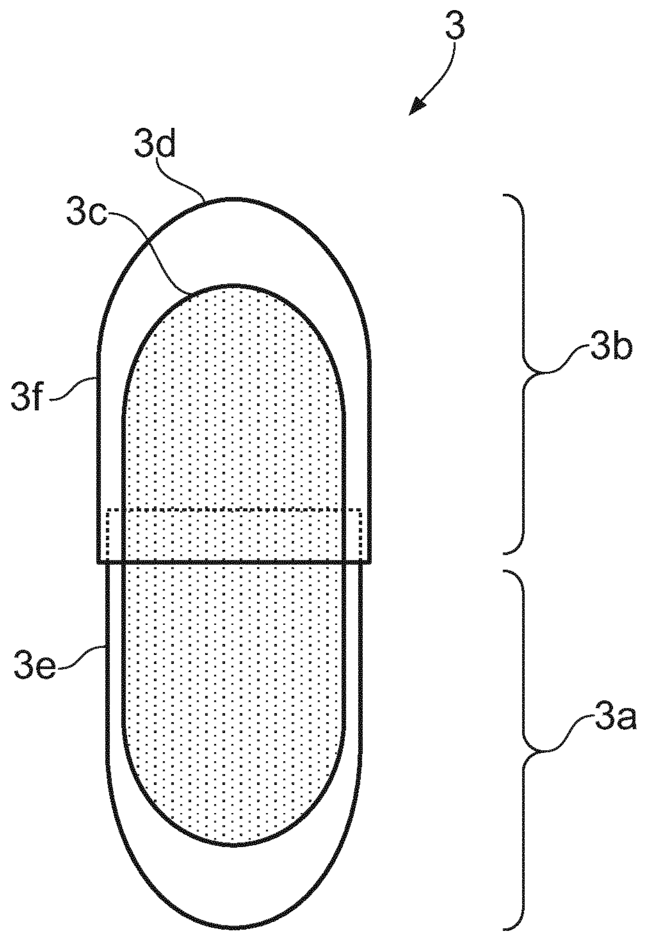
FIG. 2 is a schematic diagram of a non-limiting example of a capsule (3) showing how the inner shell (3*c*) is contained within an outer shell (3*d*) formed from two pieces, i.e. a lower diameter body (3*e*) and a greater diameter cap (3*f*).
Figure 3:
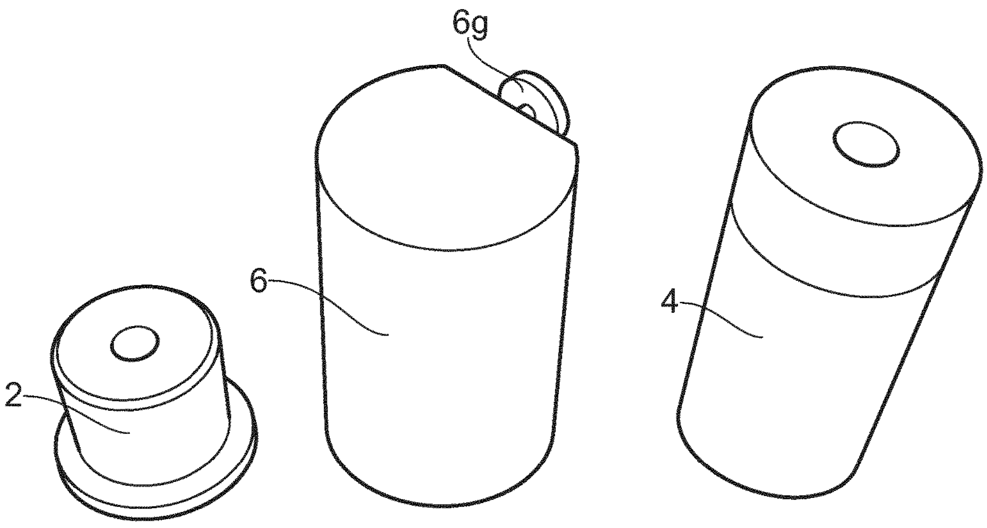
FIG. 3 depicts a non-limiting example of various components of an exemplary system of the present invention. From left to right are shown a capsule holder (2), a preliminary needle positioner (6) with a screw (6*g*) and a shielded needle positioner (4).
Figure 4:
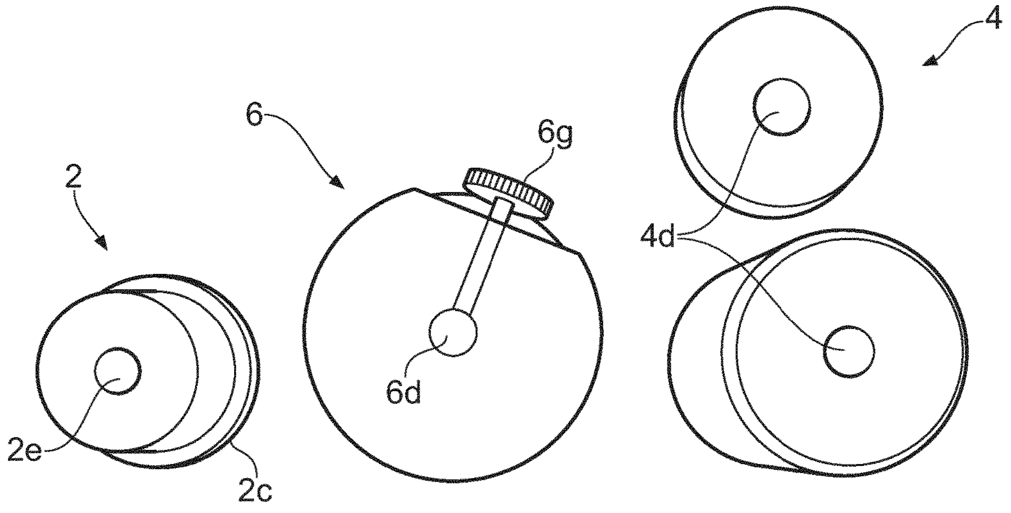
FIG. 4 depicts the system of FIG. 3 viewed from the top. The solid base (2*c*) and well (2*e*) of the capsule holder (2) can be seen. The screw (6*g*) and bore (6*d*) of the preliminary needle positioner (6) can be seen. The bore (4*d*) of the shielded needle positioner (4) can be seen. Also, in the embodiment of the shielded needle positioner illustrated, it can be appreciated that it is formed from two separate pieces, i.e. a main body and a cap. This embodiment facilitates access to the inner bore, which is useful e.g. for cleaning.
Figure 5:
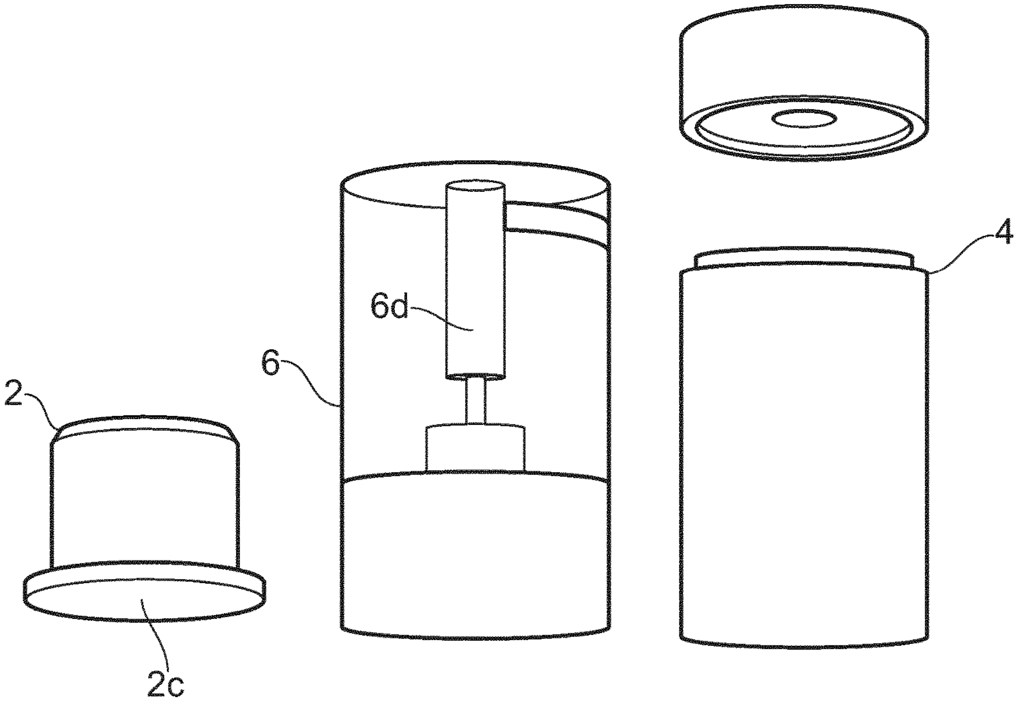
FIG. 5 shows the same components as in FIG. 4 but lying flat on a surface.
Figure 6:
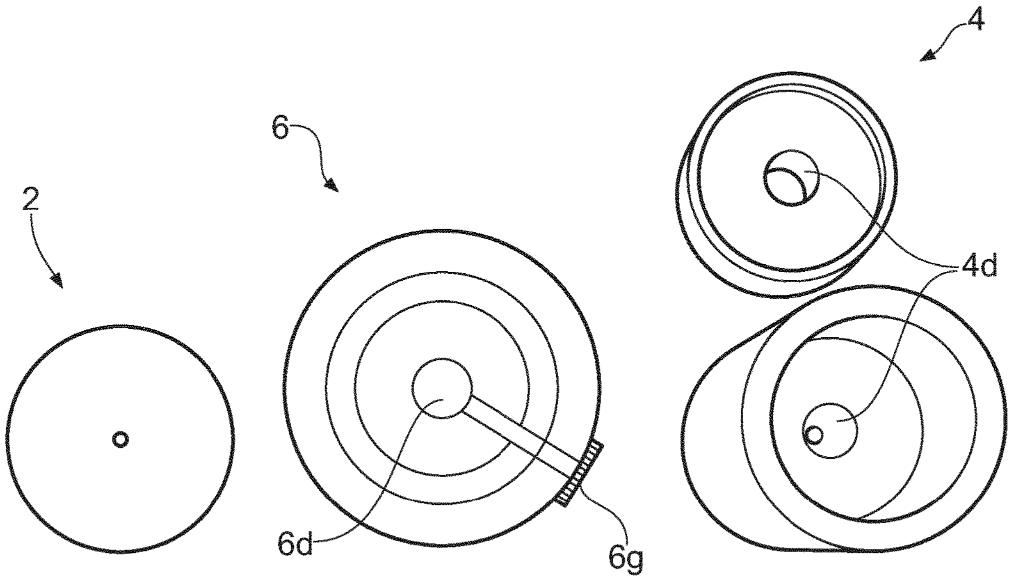
FIG. 6 is an underside view of the same components as FIG. 4.
Figure 7:
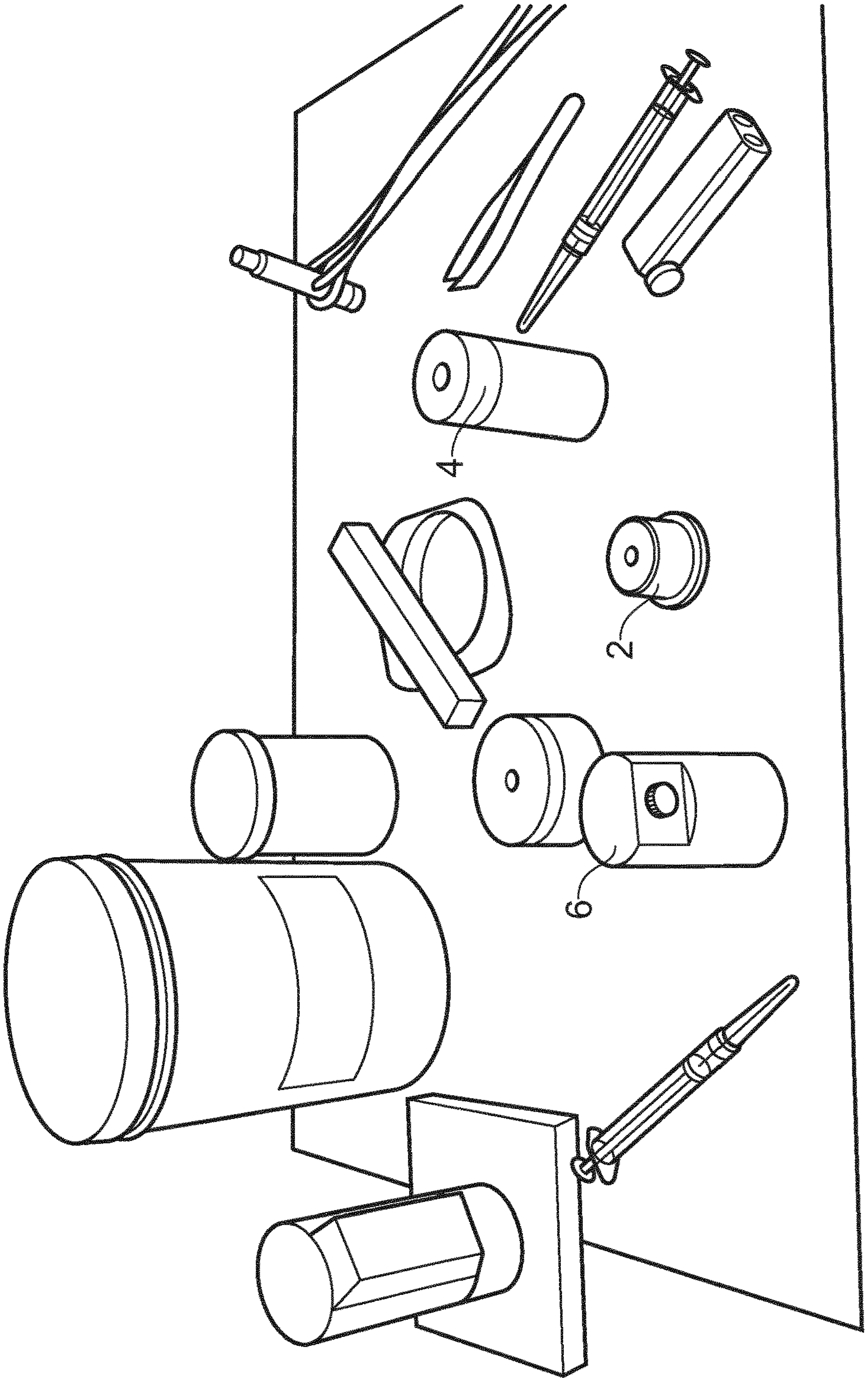
FIG. 7 shows an exemplary set up of a system of the present invention depicting the capsule holder (2), shielded needle positioner (4) and preliminary needle positioner (6) in a hot cell in preparation to carry out an embodiment of the method of the invention.

The terms "upper" and "lower" are used herein in connection with various components of the system of the invention and describe said components when positioned in a typical manner within the system of the invention, for example as illustrated in the non-limiting embodiment of FIG. 1.

The terms "extending upwardly" and "extending downwardly" take their ordinary meaning, i.e. towards a higher place and towards a lower place, respectively.

The term "well" refers to a depression or enclosed space designed to provide sufficient space to accommodate and orientate a capsule therein.

The term "radiation-shielding material" refers to any one of various high atomic number (Z) materials that absorb radiation and can be used as protection for radiation. For alpha particles where the range is very short, a very thin layer of material is sufficient. For beta particles the shielding is ideally first a layer with a material with a low atomic number, e.g. followed with a second layer of a material with a high atomic number. Gamma radiation on the other hand has is highly penetrative and therefore a highly absorbing material should be used. For economic reasons, lead (Pb) is the most commonly used for this purpose. Another material that is frequently used is tungsten (W). Tungsten has the advantage that it is a robust material, unlike lead which is relatively soft. The reader is referred for more detail to Saha G B "Physics and Radiobiology of Nuclear Medicine" (New York: Springer; 2001. p. 218).

In one embodiment of the system (1) of the invention said shielded needle positioner (4) further comprises a cap (4*g*) configured to fit over the upper end (4*b*) thereof wherein said cap comprises a bore (4*h*) therethrough having a similar width to the upper section (4*f*) of the bore (4*d*) of the shielded needle positioner (4), wherein said cap (4*g*) is formed from a radiation-shielding material.

In one embodiment of the system (1) of the invention said radiation-shielding material is comprises lead, steel or tungsten.

In one embodiment the system (1) of the invention further comprises:

(iii) a preliminary needle positioner (6) having a lower end (6*a*) and an upper end (6*b*) wherein said preliminary needle positioner (6) comprises a body (6*c*) defining a bore (6*d*) extending substantially linearly and centrally therethrough, said bore (6*d*) comprising a lower section (6*e*) opening onto said lower end (6*a*) and configured to be fitted over and contain the solid body (2*d*) of said capsule holder (2), and an upper section (6*f*) opening onto said upper end (6*b*) and configured to contain an upper half (3*b*) of a capsule (3), wherein said shielded needle positioner (6) is formed from a rigid material.

With this embodiment it is possible to vent the inner capsule with a larger bore needle first and also provide a target for injection of a solution of radioactivity thereafter. The diameter of the needle is indicated by the needle gauge. Various needle lengths are available for any given gauge. There are a number of systems for gauging needles, including the Stubs Needle Gauge and the French Catheter Scale. Smaller gauge numbers indicate larger outer diameters. Needles in common medical use range from 7 gauge (the largest) to 33 (the smallest) on the Stubs scale. An list with gauge comparison chart can e.g. be found at the following link: https://en.wikipedia.org/wiki/Needle_gauge_comparison_chart. An International Standard is available to establishes a colour code for the identification of Single-use hypodermic needles of nominal outside diameters (ISO 7864:1993 Sterile hypodermic needles for single use).

In one embodiment of the system (1) of the invention each of the components is substantially cylindrical.

In one embodiment of the system (1) of the invention said rigid material comprises a rigid plastic. A suitable plastic is one that is readily available and that can be easily crafted, e.g. by injection moulding or machining, without need to use difficult tools. In one embodiment said rigid material is transparent but this is not essential.

In one embodiment of the system (1) of the invention said rigid material comprises Perspex.

In one embodiment of the system (1) of the invention said rigid material comprises a metal.

In one embodiment of the system (1) of the invention said body (6*c*) of said preliminary needle positioner (6) is solid.

In one embodiment of the system (1) of the invention said body (6*c*) of said preliminary needle positioner (6) is a scaffold.

In one embodiment the system (1) of the invention further comprises securing means (6*g*) configured to support a needle within the bore (6*d*) of said preliminary needle positioner (6).

In one embodiment of the system (1) of the invention said securing means (6*g*) comprises a spring or a screw. Suitable examples of securing means will be evident to those of skill in the art, e.g. stainless steel springs or screws. The function is to fix the syringe in place for puncturing multiple capsules.

In one embodiment of the method of the invention steps (a)-(h) are carried out sequentially.

In one embodiment of the method of the invention said capsule (3) is suitable for oral administration.

In one embodiment of the method of the invention said capsule (3) is made from a material comprising gelatine or polymer formulated from cellulose.

In one embodiment of the method of the invention said capsule (3) is made from hard gelatine.

In one embodiment of the method of the invention said inner shell (3*c*) contains an absorbing buffer.

In one embodiment of the method of the invention said absorbing buffer comprises a hydroscopic crystalline powder.

In one embodiment of the method of the invention said absorbing buffer is dibasic sodium phosphate anhydrous USP. In a particular embodiment said absorbing buffer is around 200-500 mg dibasic sodium phosphate anhydrous USP.

In one embodiment of the method of the invention said inner shell (3*c*) contains a stabiliser.

In one embodiment of the method of the invention said stabiliser is disodium edetate dehydrate.

In one embodiment of the method of the invention said inner shell (3*c*) contains a reducing agent.

In one embodiment of the method of the invention said reducing agent is sodium thiosulfate pentahydrate.

In one embodiment of the method of the invention, at the end of said method, the pH of the contents of said inner shell (3*c*) is in the range 7.5-9.0.

In one embodiment of the method of the invention said solution of radioactivity comprises a radioactive isotope suitable for use as an orally-administered radiopharmaceutical.

The list below provides non-limiting examples of radiopharmaceuticals that are suitable for oral administration in a capsule and therefore for the present invention.

| Radiopharmaceutical | Range | Reference |
|---|---|---|
| I-123 Sodium Iodide: | 3.7 MBq-14.8 MBq | Summary of Product Characteristics (SPC) |
| I-131 Sodium Iodide: | 0.2-11 MBq diagnostic indications 200-11100 MBq therapeutic indications | Summary of Product Characteristics (SPC) |
| Tc-99m pertechnetate | 2-925 MBq | Summary of Product Characteristics (SPC) of Drytec ® |
| I-124 Sodium Iodide | 0.2-74 MBq | Freudenberg L S, Jentzen W, Petrich T, Frömke C, Marlowe R J, Heusner T, Brandau W, Knapp W H, Bockisch A. Lesion dose in differentiated thyroid carcinoma metastases after rhTSH or thyroid hormone withdrawal: $^{124}$I PET/CT dosimetric comparisons. Eur J Nucl Med Mol Imaging. 2010 December; 37(12): 2267-76. PMID: 20661558. Freudenberg L S, Jentzen W, Stahl A, Bockisch A, Rosenbaum-Krumme S J. Clinical applications of $^{124}$I-PET/CT in patients with differentiated thyroid cancer. Eur J Nucl Med Mol Imaging. 2011 May; 38 Suppl 1: S48-56. PMID: 21484380. Jentzen W, Freudenberg L, Eising E G, Sonnenschein W, Knust J, Bockisch A. Optimized $^{124}$I PET dosimetry protocol for radio-iodine therapy of differentiated thyroid cancer. J Nucl Med. 2008 June; 49(6): 1017-23. PMID: 18483099. |

However, for each individual case, the dose prescribed must be determined by the attending specialist. In an individual case the attending specialist might choose to use a activity/dose different than mentioned in the table above. This will be known to the person of skill in the art, for example as described for $^{131}$I at the following link: http://reference.medscape.com/drug/hicon-sodium-iodide-i-131-999924.

In one embodiment of the method of the invention said radioactive isotope is radioiodine or $^{99m}$Tc.

In one embodiment of the method of the invention said radioiodine is selected from the group comprising $^{123}$I, $^{131}$I and $^{124}$I. Non-limiting examples of typical doses of $^{123}$I, $^{131}$I and $^{124}$I are 3.7 MBq, 1000 MBq and 74 MBq, respectively.

In one embodiment of the method of the invention said solution of radioactivity is a solution of sodium iodide.

In one embodiment of the method of the invention said solution of radioactivity is a solution of $^{99m}$Tc pertechnetate.

In one embodiment of the method of the invention said method includes the further steps carried out in between steps (c) and (d) of:

(c-i) placing the preliminary needle positioner (6) as defined herein over the capsule holder (2);

(c-ii) introducing a second needle (7*b*) into the upper section (6*f*) of the bore (6*d*) at the upper end (6*b*) of said preliminary needle positioner (6) wherein said second needle (7*b*) has a smaller gauge compared to said first needle (7*a*);

(c-iii) optionally securing said second needle (7*b*) into place in said needle positioner;

(c-iv) piercing a hole in the top of the inner shell (3*c*) with said second needle (7*b*); and, (c-v) removing the preliminary needle positioner (6).

In one embodiment of the method of the invention said securing step (c-iii) is achieved by means of securing means (6*g*) supported within said preliminary needle positioner (6).

In one embodiment of the method of the invention said securing means (6*g*) comprises a screw or a spring.

In one embodiment the method of the invention is automated. The system of the invention comprises components of regular shape and size and the method is easily definable in time and space. As such, a person of skill in the art would have no difficulty in automating the system and method of the present invention. Automation of the method of the present invention would be convenient in a radiopharmacy filling in the region of up to 10 oral capsules per day.

This written description uses examples to disclose the invention, including the best mode, and also to enable any person skilled in the art to practice the invention, including making and using any devices or systems and performing any incorporated methods. To more clearly and concisely describe and point out the subject matter of the claimed invention, definitions are provided herein for specific terms used throughout the present specification and claims. Any exemplification of specific terms herein should be considered as a non-limiting example. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

EXAMPLES

Example 1

Evaluation of Capsule Filling Shield

Introduction:

A study was performed to compare the known manual method with the method using an exemplary system of the invention. 10 capsules were filled with a solution of Tc-99m pertechnetate (obtained from a Drytec® generator) using the manual technique and 10 capsules were filled using an exemplary method of the invention. The time required for the actual filling process of the capsule was recorded. After the capsules were filled the activity of each capsule was measured in a dose calibrator (Veenstra).

Results:

The method with the method of the invention was for the actual filling process faster. The results are summarized in the table below. The method with the method of the invention proved to be twice as fast as manual filling.

Time to fill 10 capsules manual and with the present invention

| | Manual | Invention | Difference |
|---|---|---|---|
| Time for filling (s) | 23.62 ± 08.37 | 10.26 ± 03:91 | 13.36 faster |

Values represent time in seconds (mean ± SD);
n = 10

Figure 8:
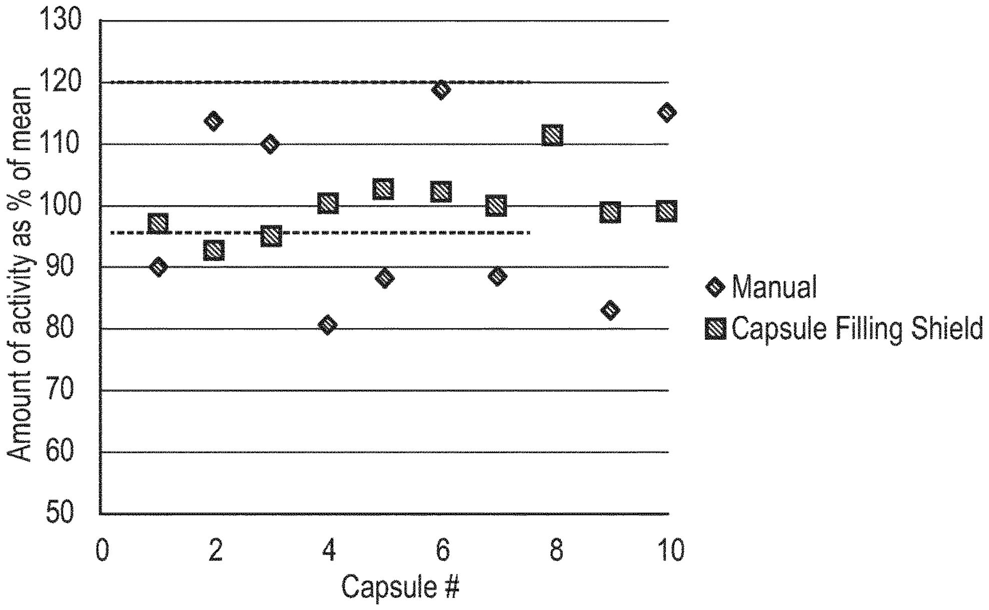
FIG. 8 is a graph showing uniformity of the activity of capsules obtained using an exemplary method of the present invention ("Capsule Filling Shield") as compared with the prior art method.

The uniformity of the capsules was determined by measuring the activity (the patient dose) per capsule. The results are plotted in FIG. 8 (wherein the exemplary system of the invention is referred to as "Capsule Filling Shield") and summarized in the table below. Using USP guidelines <905> it was shown that for 10 capsules the manual method did not pass the criteria mentioned in USP for 10 units. The method of the invention in contrast did meet these requirements.

Uniformity of content for manual method and with the present invention

| | Manual | With CFS |
|---|---|---|
| Activity | 74.41 ± 6.34 | 74.13 ± 3:68 |
| All activities within ≥85% and ≤115% range & RSD <6% | No | Yes |

Values represent activity in MBq (mean ± SD);
n = 10

Conclusion:

It was shown that the method of the invention made the filling process of the capsules twice as fast. Operators also reported reduced chances of spills or needle stick injuries. Regarding the uniformity of the capsules it was shown that the method of the invention produced capsules meeting the USP guidelines. The inventive method gave a better uniformity of the capsules compared with the known manual method.

Example 2

Evaluation of Radiation Exposure Capsule Filling Shield

Introduction:

A calculation was done to show the effect on extremity radiation exposure. The calculation was done for three Iodine isotopes, as these isotopes are mostly used for compounding capsules in nuclear pharmacies. The three Iodine isotopes chosen were: I-123, I-124 and I-131. In the calculation activity of 3.7 MBq for I-123, 74 MBq for I-124 and 1000 MBq for I-131 are chosen. These represent normal patient doses.

Figure 9:
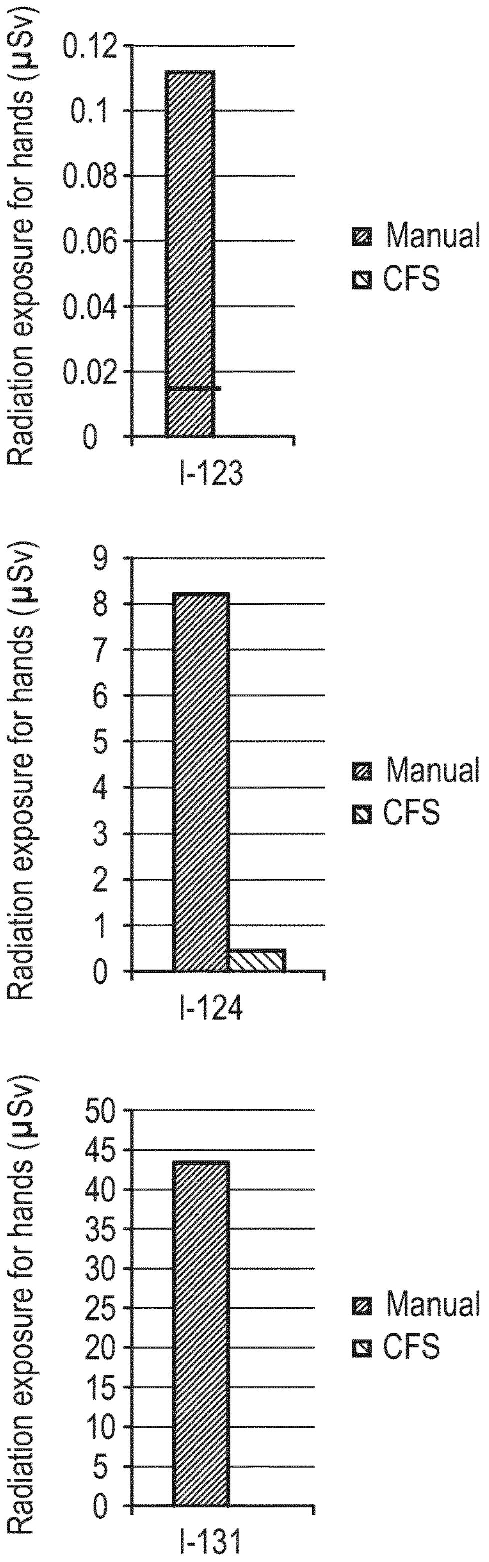
FIG. 9 shows radiation exposure to hands for the prior art method compared with an exemplary method of the invention ("CFS").

Results:

The radiation exposure of the hands was calculated for the manual method and the exemplary method of the invention. The results are mentioned in the tables below and plotted in FIG. 9 (the invention referred to in FIG. 9 as "CFS", which stands for capsule filling shield).

| Manual | | Distance to | Time | Dose Rate Constant (μSv/h | Shielding | Halflayer | Radiation exposure |
|---|---|---|---|---|---|---|---|
| Nuclide | Activity (MBq) | source (cm) | to fill (s) | per MBq/m2) | (cm Tungsten) | value (cm) | for hands (μSv) |
| I-123 | 3.7 | 10 | 23.62 | 0.046 | 0 | 0.1 | 0.11 |
| I-124 | 74 | 10 | 23.62 | 0.17 | 0 | 0.5 | 8.25 |
| I-131 | 1000 | 10 | 23.62 | 0.066 | 0 | 0.2 | 43.30 |

| Invention | | Distance to | Time | Dose Rate Constant (micro Sv/h | Shielding | Halflayer | Radiation exposure |
|---|---|---|---|---|---|---|---|
| Nuclide | Activity (MBq) | source (cm) | to fill | per MBq/m2) | (cm Tungsten) | value (cm) | for hands (μSv) |
| I-123 | 3.7 | 10 | 10.74 | 0.046 | 1.5 | 0.1 | 1.55E10−6 |
| I-124 | 74 | 10 | 10.74 | 0.17 | 1.5 | 0.5 | 0.47 |
| I-131 | 1000 | 10 | 10.74 | 0.066 | 1.5 | 0.2 | 0.11 |

Conclusion:

The radiation exposure to hands was calculated for two methods of filling of capsules. Faster filling and extra shielding with the method of the present invention contributed to a considerable decrease in radiation exposure to the hands. For I-123 the radiation exposure was reduced to almost zero. For I-131 the radiations exposure was reduced a factor 394. For I-124 the radiations exposure was reduces a factor 17.5. The present invention therefore proves to reduce radiation burden on hands.

The invention claimed is:

1. A system comprising:

(i) a capsule holder having a lower end and an upper end wherein said capsule holder comprises a solid base positioned at said lower end, a solid body extending upwardly from said solid base, and a well extending downwardly within said solid body wherein said well opens at the upper end of said capsule holder and ends prior to said solid base and is configured to receive a lower half of a capsule, wherein said capsule holder is formed from a radiation-shielding material; and (ii) a shielded needle positioner having a lower end and an upper end wherein said shielded needle positioner comprises a solid body defining a bore extending substantially linearly and centrally therethrough, said bore comprising a lower section opening onto said lower end and configured to be fitted over and contain the solid body of said capsule holder, and an upper section opening onto said upper end and configured to receive an upper half of a capsule, wherein said shielded needle positioner is formed from a radiation-shielding material.

2. The system of claim 1, wherein said shielded needle positioner further comprises a cap configured to fit over the upper end thereof wherein said cap comprises a bore therethrough having a similar width to the upper section of the bore of the shielded needle positioner, wherein said cap is formed from a radiation-shielding material.

3. The system of claim 1, wherein the radiation-shielding material comprises lead, steel or tungsten.

4. The system of claim 1, further comprising:

(iii) a preliminary needle positioner having a lower end and an upper end wherein said preliminary needle positioner comprises a body defining a bore extending substantially linearly and centrally therethrough, said bore comprising a lower section opening onto said lower end and configured to be fitted over and contain the solid body of said capsule holder, and an upper section opening onto said upper end and configured to contain an upper half of a capsule, wherein said shielded needle positioner is formed from a rigid material.

5. The system of claim 4, wherein said rigid material comprises a rigid plastic.

6. The system of claim 4, wherein said rigid material comprises Perspex™.

7. The system of claim 4, wherein said body of said preliminary needle positioner is solid.

8. The system of claim 4, wherein said body of said preliminary needle positioner is a scaffold.

9. The system of claim 4, further comprising securing means configured to support a needle within the bore of said preliminary needle positioner.

10. The system 9, wherein said securing means comprises a spring or a screw.

11. The system of claim 1, wherein each of the components is substantially cylindrical.

12. A method for filling a capsule with radioactivity wherein said capsule comprises an inner shell and an outer shell wherein said outer shell comprises a lower diameter body and a greater diameter cap and wherein said method comprises the following steps:

(a) providing the system as defined in claim 1;

(b) placing said lower diameter body into the well of the capsule holder;

(c) placing said inner shell into said lower diameter body;

(d) placing the shielded needle positioner over the capsule holder containing the lower diameter body and the inner shell so that the solid body of the capsule holder is contained within the lower section of the bore of the shielded needle positioner and an upper half of the inner shell is contained within the upper section of the bore of the shielded needle positioner;

(e) introducing a first needle attached to a shielded syringe containing a solution of radioactivity into the upper section of the bore at the upper end of said shielded needle positioner;

(f) injecting the solution of radioactivity into the inner shell (g) removing the shielded needle positioner; and (h) fixing said greater diameter cap to said lower diameter body so that said inner shell is securely contained within said outer shell.

13. The method of claim 12, wherein steps (a)-(h) are carried out sequentially.

14. The method of claim 12, wherein said capsule is suitable for oral administration.

15. The method of claim 12, wherein said capsule is made from a material comprising gelatine or polymer formulated from cellulose.

16. The method of claim 15, wherein said capsule is made from hard gelatine.

17. The method of claim 12, wherein said inner shell contains an absorbing buffer.

18. The method of claim 17, wherein said absorbing buffer comprises a hydroscopic crystalline powder.

19. The method of claim 17, wherein said absorbing buffer is dibasic sodium phosphate anhydrous USP.

20. The method of claim 12, wherein said inner shell contains a stabiliser.

21. The method of claim 20, wherein said stabiliser is disodium edetate dehydrate.

22. The method of claim 12, wherein said inner shell contains a reducing agent.

23. The method of claim 22, wherein said reducing agent is sodium thiosulfate pentahydrate.

24. The method of claim 12, wherein at the end of said method, the pH of the contents of said inner shell is in the range 7.5-9.0.

25. The method of claim 12, wherein said solution of radioactivity comprises a radioactive isotope suitable for use as an orally-administered radiopharmaceutical.

26. The method of claim 25, wherein said radioactive isotope is radioiodine or $^{99m}$Tc.

27. The method of claim 26, wherein said radioiodine is selected from the group comprising $^{123}$I, $^{131}$I and $^{124}$I.

28. The method of claim 12, wherein said solution of radioactivity is a solution of sodium iodide.

29. The method of claim 12, wherein said solution of radioactivity is a solution of $^{99m}$Tc pertechnetate.

30. The method of claim 12, wherein the system further comprising:

(iii) a preliminary needle positioner having a lower end and an upper end wherein said preliminary needle positioner comprises a body defining a bore extending substantially linearly and centrally therethrough, said bore comprising a lower section opening onto said lower end and configured to be fitted over and contain the solid body of said capsule holder, and an upper section opening onto said upper end and configured to contain an upper half of a capsule, wherein said shielded needle positioner is formed from a rigid material, wherein said method further comprising between steps (c) and (d) steps of:

(c-i) placing the preliminary needle positioner over the capsule holder;

(c-ii) introducing a second needle into the upper section of the bore at the upper end of said preliminary needle positioner wherein said second needle has a smaller gauge compared to said first needle;

(c-iii) optionally securing said second needle into place in said needle positioner;

(c-iv) piercing a hole in the top of the inner shell with said second needle; and, (c-v) removing the preliminary needle positioner.

31. The method of claim 30, wherein said securing step (c-iii) is achieved by means of securing means supported within said preliminary needle positioner.

32. The method of claim 31, wherein said securing means comprises a screw or a spring.

33. The method of claim 12, wherein the method is automated.

* * * * *